United States Patent [19]

Abramovich

[11] 4,227,411
[45] Oct. 14, 1980

[54] RELATIVE HUMIDITY MEASUREMENT

[75] Inventor: Abe Abramovich, Lawrenceville, N.J.

[73] Assignee: RCA Corporation, New York, N.Y.

[21] Appl. No.: 77,913

[22] Filed: Sep. 24, 1979

[51] Int. Cl.$^3$ .......................................... G01N 31/00
[52] U.S. Cl. .................................. 73/336.5; 73/17 A; 73/29; 338/35
[58] Field of Search ...................... 73/336.5, 29, 17 A; 338/35; 340/602

[56] References Cited

U.S. PATENT DOCUMENTS

| | | | |
|---|---|---|---|
| 3,204,418 | 9/1965 | Mathews | 73/336.5 |
| 3,319,457 | 5/1967 | Leone | 73/17 A |
| 3,864,659 | 2/1975 | Furuuchi et al. | 338/35 |
| 3,902,040 | 8/1975 | Ikeda et al. | 73/336.5 |
| 4,052,691 | 10/1977 | Nagano et al. | 338/35 |

*Primary Examiner*—Donald O. Woodiel
*Attorney, Agent, or Firm*—Samuel Cohen; Carl V. Olson

[57] ABSTRACT

A relative humidity measuring instrument includes two spaced electrodes on an insulating substrate which is mounted on a Peltier-effect thermoelectric module. When the substrate is cooled by the thermoelectric module, a comparator connected to the electrodes on the substrate detects a decrease in resistance between said electrodes due to condensation of moisture therebetween. Then a microcomputer receptive to temperature signals from a thermometer on the substrate and an ambient thermometer computes the relative humidity.

9 Claims, 1 Drawing Figure

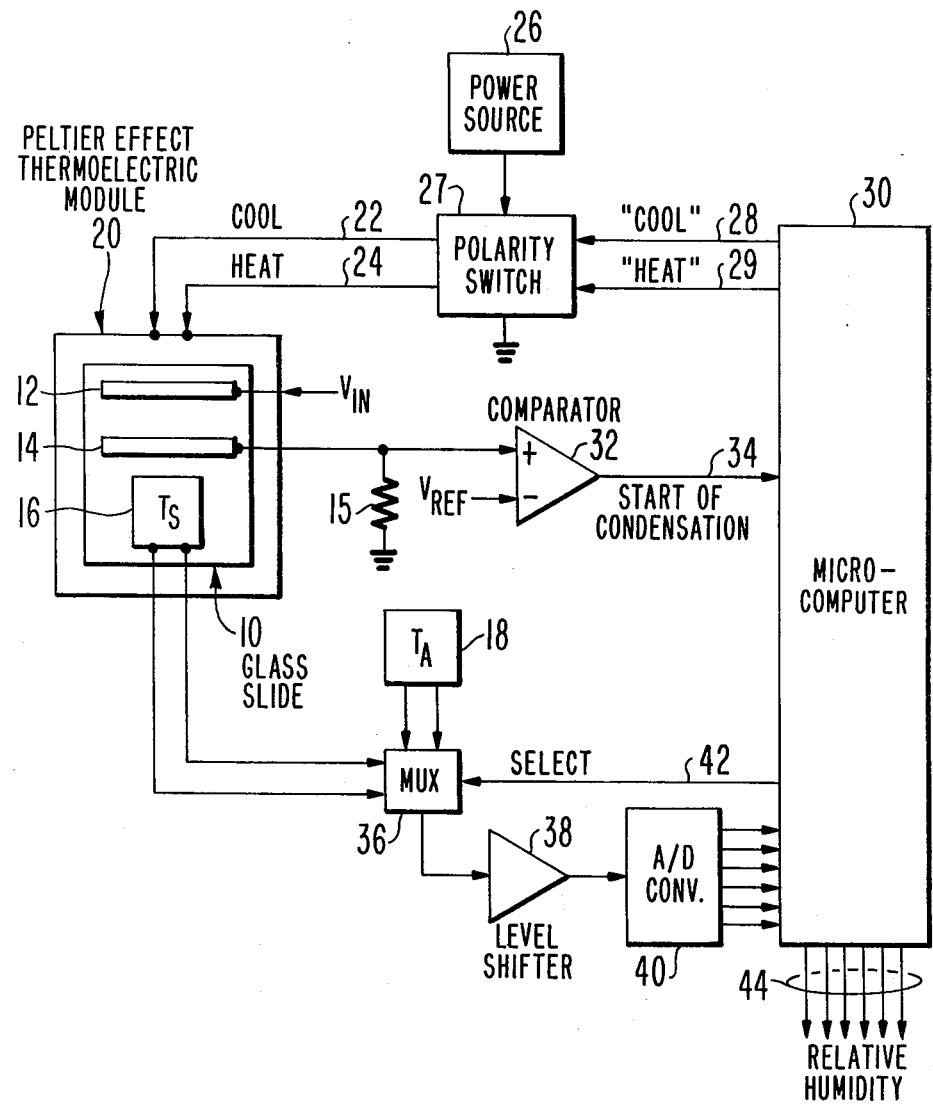

RELATIVE HUMIDITY MEASUREMENT

This invention relates to relative humidity measuring instruments, and particularly to automatic, electronic, digital, humidity measuring instruments suitable for inclusion in large air conditioning systems.

In accordance with an example of the invention, an insulating substrate provided with two spaced electrodes is mounted on a Peltier-effect thermoelectric module which heats and then cools the substrate under control of a microcomputer. A comparator connected to the electrodes detects a drop in resistance therebetween due to condensation of moisture, and then, substrate and ambient thermometers provide signals to the microcomputer which computes the relative humidity.

In the drawing:

The sole FIGURE of the drawing is a relative humidity measuring instrument constructed according to the teachings of the invention.

Referring now in greater detail to the drawing, an insulating substrate 10 in the form of a glass slide is provided on its top surface with spaced electrodes 12 and 14 separated by a distance of typically between 0.05 and 0.20 mm. Any known construction may be employed, such as described in U.S. Pat. Nos. 3,864,659 to Furuuchi et al. and 4,052,691 to Magano et al. A substrate thermometer 16 is mounted on the glass slide near the electrodes to provide an electrical signal representing the temperature ($T_s$) of the glass slide. An ambient thermometer 18 is mounted nearby to provide an electrical signal representing the temperature ($T_A$) of the ambient air having a humidity which is to be measured. The thermometers produce voltages which are proportional to temperature, and may be type AD590J temperature transducers manufactured by Analog Devices, Inc.

The glass slide substrate 10 is mounted on a Peltier-effect thermoelectric module 20 by means of a thermally conductive grease. The module 20 may be a Cambrian 801-2001-01 unit made by Cambridge Thermionic Corp., Cambridge, Mass. A thermoelectric module consists of a thermoelectric material sandwiched between two ceramic panels and connected by two wires 22 and 24 to the exterior. When an electric direct current is caused to flow from wire 22 into the module 20 and out the wire 24, the surface of the module on which the glass substrate 10 is mounted is cooled. And, when an electric current is caused to flow in the opposite direction from wire 24 into the module, the same surface gives off heat. The direction of current 20 from a power source 26 is controlled by a polarity switch 27, which is in turn controlled by "cool" and "heat" command signals applied over lines 28 and 29 from a microcomputer 30. The polarity switch may be simply an electronic equivalent of a double-pole, double-throw switch. The microcomputer may, for example, be a Model 8048 unit manufactured by Intel Corporation.

A source (not shown) of a fixed voltage $V_{in}$ is connected to electrode 12 on the glass substrate 10. The other electrode 14 is connected to a voltage divider resistor 15 and to the non-inverting input of a comparator 32. A reference voltage $V_{ref}$ lower than the voltage $V_{in}$ is connected from a source (not shown) to the inverting input of the comparator 32. When the voltage at the noninverting input of comparator 32 exceeds $V_{ref}$, a signal pulse is supplied over line 34 to microcomputer 30. The comparator 32 may be a Type CA3290 unit made by RCA Corporation.

The signal outputs of substrate thermometer 16 and the ambient thermometer 18 are connected through a multiplexer 36, a level shifter 38 and an analog-to-digital converter 40 to the microcomputer 30. The multiplexer 36 and the converter 40 may be constituted by a Type ADC0816 unit made by National Semiconductor Corp. Command signals applied over line 42 from the microcomputer 30 to the multiplexer determine the time when temperature signals are passed, in sequence, from the two thermometers to the microcomputer.

In the operation of the humidity measuring apparatus in the drawing, the microcomputer first issues a "cool" command over line 28 to the polarity switch 27. This causes current from the power source 26 to flow through line 22 to thermoelectric module 20 and back out through line 24. The current flow in this direction causes the module to cool the glass substrate 20 until the dew point is reached and moisture is condensed on the glass substrate. The moisture lowers the resistance between electrode 12 and electrode 14, until the voltage on electrode 14 and on the non-inverting input of comparator 32 exceeds the reference voltage $V_{ref}$. Then, the output at 34 from the comparator 32 switches from one binary state to the other state, and this change is conveyed to the microcomputer 30.

The microcomputer thereupon enters into the execution of a stored program which interrupts the flow of current for cooling to the thermoelectric module 20. The program then immediately acts over output line 42 to cause the signals representing the substrate and ambient temperatures to be sequentially transferred through multiplexer 36, level shifter 38 and analog-to-digital converter 40 to the microcomputer. The program then computes the relative humidity of the ambient air from the two temperatures using any suitable formula, such as the one taken from the ASHRAE Handbook and Product Directory, 1977, Fundamentals, Chap. 5, by American Society of Heating and Refrigerating and Air Conditioning Engineers, Inc., and described in Appendix A of the present application. The computed relative humidity value, in multi-bit form, is supplied from the microcomputer over output lines 44.

The microcomputer then issues a "heat" command over line 29 to the polarity switch 28 to raise the temperature of the glass substrate 10 and thereby rapidly evaporate the condensate in preparation for a next repeated cycle of operation in which the substrate is again cooled until moisture condenses thereon. The cycles of operation may be repeated at any desired frequency.

While a microcomputer, such as the Model 8048 unit manufactured by Intel Corporation, permits the relative humidity measurements to be completed and displayed very quickly and very frequently, simpler forms of computers may be utilized. For example, an ordinary industrial clock timer may be used to control the application of current in the "heat" direction to the thermoelectric module 20 for a predetermined period of time, followed by current in the "cool" direction for a predetermined period of time. The timer can cause energization of the comparator 32 during the cooling period, and a simple gate or switch arrangement can respond to an output of the comparator 32 to make the outputs of the thermometers 16 and 18 available for the determination of relative humidity by any suitable means, including reference to a chart or table.

APPENDIX A

Calculation for rel hum. given t (dry bulb temp °C.) and $t_d$ (dew point temp °C.)

Notation and relationships from ASHRAE Handbook and Product Directory 1977 Fund. (Chap. 5).

$$\phi_{(rel.\ hum)} = \frac{p_w}{p_{ws}}\bigg|_{t,p} \qquad \text{eq. 24}$$

Note:

$p_{ws}$ = sat. vapor press
$p_w$ = partial vapor pressure of water vapor $$\log_{10}\left(\frac{p_{ws}}{218.167}\right) = \frac{-\beta}{T}\left(\frac{a + b\beta + c\beta^3}{1 + d\beta}\right) \qquad \text{eq. 6}$$

where $p_{ws}$ = sat. press. in atmospheres
$\beta = 647.27 - T$
$T$ = abs. temp. Kelvin = $273.15 + t$ where t is in degrees C.
$a = 3.2437814$, $b = 5.86826 \times 10^{-3}$,
$c = 1.1702379 \times 10^{-8}$, $p_w$ at $t+p$ is same as $p_{ws}$ at $t_d + p$ So need only calculate $p_{ws}$ at $t_d$ & p, and $p_{ws}$ at t & p using eq. 6.

Example: Assume $t_d = 20°$ C. and $t = 30°$ C.
For $p_w$, $T_d = 293.15°$ k.; for $p_{ws}$, $T = 303.15°$ k. Subst. into eq. 6

$p_w = 0.0230562$
$p_{ws} = 0.0418407$
Rel. Hum. = $p_w/p_{ws} = 0.5510472$
% rel. hum = 55%

What is claimed is:

1. A relative humidity measuring instrument, comprising two spaced electrodes on an insulating substrate,
   a substrate thermometer and an ambient thermometer,
   means to cool, and then heat, said substrate,
   a comparator connected to said electrodes to detect a decrease in resistance between said electrodes due to condensation of moisture therebetween, and
   a computer receptive to temperature signals from said thermometers and operative in response to an output from said comparator to compute the relative humidity.

2. An instrument according to claim 1 wherein said means to cool and heat said substrate is a Peltier-effect thermo-electric module through which current in one direction causes heating and current in the opposite direction causes cooling.

3. An instrument according to claim 2 wherein said means to cool and heat said substrate includes a power supply and a polarity switch controlled by said computer.

4. An instrument according to claim 1 wherein said comparator includes means to apply a fixed voltage from one of said electrodes, across said substrate to the other electrode and to the input of a threshold detector having an output coupled to said computer.

5. An instrument according to claim 1 and including a multiplexer to connect temperature signals from said substrate and ambient thermometers to said computer under control of a command signal from said computer.

6. An instrument according to claim 5 and including an analog-to-digital converter in the temperature signals path from said multiplexer to said computer.

7. A relative humidity measuring instrument comprising, in combination:

a substrate which when cooled to the dew point of the ambient air, causes moisture to condense on a surface thereof;
   a pair of electrodes spaced from one another on said surface of said substrate;
   means for cooling the substrate at least to the point at which moisture condenses thereon;
   means coupled to said electrodes for producing a control signal when the resistance between said electrodes reduced to a given value in response to said moisture condensation;
   first temperature measuring means for producing a first output signal indicative of the temperature of the substrate; and
   second temperature measuring means for producing a second output signal indicative of the temperature of the ambient air, the humidity of which is to be measured;
   whereby, said first and second output signals can be used upon the occurrence of said control signal to determine the relative humidity of said ambient air.

8. A relative humidity measuring instrument as set forth in claim 7, further including means for heating the substrate after the control signal is produced to evaporate the moisture therefrom, and means for repeating the cooling and heating at desired intervals to obtain successive outputs indicative of relative humidity.

9. A relative humidity measuring instrument as set forth in claim 7, wherein said means for producing a control signal comprises:

means for applying a reference voltage to one of said electrodes;
   an impedance connected between the other electrode and a point of reference potential; and
   means for detecting when the voltage across said impedance reaches a given level.

* * * * *